US007358051B2

(12) United States Patent
Gianchandani et al.

(10) Patent No.: US 7,358,051 B2
(45) Date of Patent: Apr. 15, 2008

(54) LIQUID FLOW ACTUATION AND SUSPENSION MANIPULATION USING SURFACE TENSION GRADIENTS

(75) Inventors: Yogesh B. Gianchandani, Ann Arbor, MI (US); Amar S. Basu, Troy, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 11/446,615

(22) Filed: Jun. 5, 2006

(65) Prior Publication Data

US 2007/0281304 A1 Dec. 6, 2007

(51) Int. Cl.
*C12Q 1/68* (2006.01)

(52) U.S. Cl. ........................................ 435/6; 435/286.5

(58) Field of Classification Search .................... 435/4, 435/6, 7.1, 7.92, 287.1–287.3; 422/50, 55, 422/63; 436/514
See application file for complete search history.

(56) References Cited

U.S. PATENT DOCUMENTS

| | | | |
|---|---|---|---|
| 6,386,680 B1 | 5/2002 | Sharma et al. | 347/48 |
| 6,692,145 B2 | 2/2004 | Gianchandani et al. | 374/185 |
| 2002/0031835 A1 | 3/2002 | Schwartz | 436/180 |

OTHER PUBLICATIONS

Basu et al. "Microthermal Techniques for Mixing, Concentration, and Harvesting of DNA and other Microdroplet Suspensions", Ninth International Conference Miniaturized Chemical and Biochemical An (MicroTAS 2005), pp. 131-134 (Oct. 2005).*

Basu et al., "Trapping and Manipulation of Particles and Droplets Using Micro-Toroidal Convection Currents", IEEE International Conference on Solid-State Sensors and Actuators (Transducers), pp. 85-88 (Jun. 5, 2005).*

Basu et al., "High Speed Microfluidic Doublet Flow in Open Pools Driven by Non-Contact Micromachined Thermal Sources," *IEEE/ASME International Conference on Micro Electro Mechanical Systems* (*MEMS 2005*), pp. 666-669 (Feb. 2005).

Basu et al., "Microthermal Techniques for Mixing, Concentration, and Harvesting of DNA and Other Microdroplet Suspensions," *Ninth International Conference Miniaturized Chemical and Biochemical An* (*MicroTAS 2005*), pp. 131-134 (Oct. 2005).

Basu et al., "Trapping and Manipulation of Particles and Droplets Using Micro-Toroidal Convection Currents," *IEEE International Conference on Solid-State Sensors and Actuators* (*Transducers*), pp. 85-88 (Jun. 5, 2005).

Cazabat et al., "Fingering Instability of Thin Spreading Files Driven by Temperature Gradients," *Nature*, vol. 346, pp. 824-826 (1990).

Darhuber et al., "Microfluidic Actuation by Modulation of Surface Stresses," *App. Phys. Lett.*, vol. 82, No. 4, pp. 657-659 (2003).

Deegan et al., "Contact Line Deposits in an Evaporating Drop," *The American Physical Review E*, vol. 62, No. 1, pp. 756-765 (2000).

Katsura et al., "Micro-Reactors Based on Water-In-Oil Emulsion," *IEEE Ind. Applications Conf./IAS Annual Meeting*, pp. 1124-1129 (1999).

Li et al., "Applications of a Low Contact Force Polyimide Shank Bolometer Probe for Chemical and Biological Diagnostics," *Sensors and Actuators A*, vol. 104, pp. 236-245 (2003).

Truskett et al., "Influence of Surfactants on an Evaporating Drop: Fluorescence Images and Particle Deposition Patterns," *Langmuir*, vol. 19, pp. 8271-8279 (2003).

* cited by examiner

*Primary Examiner*—Ann Y Lam
(74) *Attorney, Agent, or Firm*—Marshall, Gerstein & Borun LLP

(57) ABSTRACT

Disclosed herein is a method of collecting suspensions in a liquid film including the steps of developing a variation in surface tension at a gas-liquid interface of the liquid film to generate a circulating flow pattern within the liquid film, and scanning the liquid film with the circulating flow pattern for entrapment of the suspensions in the flow pattern by re-directing the variation in the surface tension across the gas-liquid interface of the liquid film.

34 Claims, 5 Drawing Sheets

32
38
36
Collection Area
XY Scanning Stage
Heat Source
34
34
40

LIQUID FLOW ACTUATION AND SUSPENSION MANIPULATION USING SURFACE TENSION GRADIENTS

STATEMENT REGARDING FEDERALLY SPONSORED RESEARCH OR DEVELOPMENT

This invention was made with government support under Contract No. 043899 awarded by the National Science Foundation. The government has certain rights in the invention.

BACKGROUND OF THE DISCLOSURE

1. Field of the Disclosure

The disclosure relates generally to liquid flow actuation and control techniques and, more particularly, to the use of variations in surface tension in such techniques.

2. Brief Description of Related Technology

Microfluidic actuation techniques have been actively researched for use in biochemical assays and other applications. Droplet actuation techniques have generally relied upon surface forces (i.e., surface energy gradients), and have typically been implemented using electrowetting, temperature gradient, chemical surface gradient, and dielectrophoresis techniques. For instance, the surface energy gradients can be created by adjusting the relative degree to which an underlying surface is hydrophilic or hydrophobic. Surface forces can create flow in continuous films as well, using electrochemically generated surfactants, but at the expense of liquid contamination.

Other past work has studied Marangoni flows generated by contact heating a liquid film from below, causing hexagonal flow cells to be created in a spatially periodic manner. See, for example, Getling et al., "Cellular Flow Patterns and their Evolutionary Scenarios in Three-dimensional Rayleigh-Benard Convection," *Phys. Rev. E.*, vol. 67, pp. 46313/1-46313/4 (2003).

Generally speaking, past surface force-based and other microfluidic techniques have utilized patterned substrates or prefabricated microchips. Such microchips are often assay- or application-specific, which may restrict the use or scope of the techniques. Moreover, microchips, as prefabricated structures, generally lack the capability to be reconfigured.

Oil is being increasingly used as a liquid phase in biological and chemical analysis systems. Microdroplets of water emulsified in oil have been used as micro-scale chemical reactors in several applications including the concentration of dissolved solutes and nanoparticles, as well as the amplification of single DNA molecules. The low evaporation rates of oil make it a desirable collection medium for long-term non-toxic sampling of airborne bioparticulates, and its optical transparency has made it popular as a liquid medium for micro-droplet based embryo culture.

Within the context of microfluidic systems, prior work has focused on how to generate microdroplets of water within a continuous oil phase and manipulate them (one at a time) using electrophoretic or optical forces. For example, lasers and electrostatic probes have been proposed as tools for droplet manipulation. See, for example, Ashkin, "Application of Radiation Pressure," *Science*, vol. 210, pp. 1081-1087 (1980).

Recent work has also been directed to flow manipulation in water. See Basu et al., "High Speed Microfluidic Doublet Flow in Open Pools Driven by Non-Contact Micromachined Thermal Sources," *Proc. Intl. Conf. on Micro Electro Mechanical Sys*., Miami Beach, Fla., pp. 666-669 (February 2005). In this work, a micro-scale heat source was suspended above water to generate a high-speed doublet pattern.

SUMMARY OF THE DISCLOSURE

In accordance with one aspect of the disclosure, a method is useful for collecting suspensions in a liquid film. The method includes the steps of developing a variation in surface tension at a gas-liquid interface of the liquid film to generate a circulating flow pattern within the liquid film, and scanning the liquid film with the circulating flow pattern for entrapment of the suspensions in the flow pattern by re-directing the variation in the surface tension across the gas-liquid interface of the liquid film.

In some cases, the suspensions include emulsified droplets. The method may then further include the step of maintaining the variation in the surface tension at the gas-liquid interface to merge the emulsified droplets entrapped in the circulating flow pattern.

In some embodiments, the developing step includes projecting a thermal flux toward the gas-liquid film. The method may then further include the step of enhancing evaporation of the liquid by maintaining the projecting step. The evaporation enhancing step may then include forming residue from the suspensions at a concentration location. The evaporation enhancing step may also include directing an atomic force microscopy (AFM) probe as a heat source toward the concentration location. In such cases, the method further includes the step of obtaining an image using the AFM probe of the residue at the concentration location.

The method may alternatively further include the step of collecting the suspensions by exposing the entrapped suspensions to a collection apparatus having receptors configured to collect the suspensions. In some cases, the receptors include ligand molecules, and the suspensions include DNA molecules.

In some embodiments, the circulating flow pattern includes a toroidal cell.

In some embodiments, the liquid includes an oil.

In accordance with another aspect of the disclosure, a method is useful for controlling flow in a non-aqueous liquid film. The method includes the steps of developing a variation in surface tension at a gas-liquid interface of the non-aqueous liquid film, and generating a flow pattern within the non-aqueous liquid film by maintaining the surface tension variation at the gas-liquid interface of the non-aqueous liquid film.

In some cases, the developing step includes the step of projecting a thermal flux toward the gas-liquid interface of the non-aqueous liquid from a source suspended above the gas-liquid interface of the non-aqueous liquid. The projecting step may then include the step of positioning a thermal probe in proximal relation to the gas-liquid surface.

In some embodiments, the developing step includes the step of modifying the surface tension at the gas-liquid interface with an electric field.

The developing step may include the step of suspending a probe above the gas-liquid interface. In such cases, the method further includes the step of re-positioning the probe to move the flow pattern across the non-aqueous liquid film. The method may then further include the step of entrapping suspensions in the non-aqueous liquid film within the flow pattern. The method may still further include the step of depositing the entrapped suspensions in receptors configured to collect the entrapped suspensions.

In some embodiments, the non-aqueous liquid includes an oil. Aqueous droplets may then be emulsified in the oil and trapped within the flow pattern. The generating step may include the step of merging the aqueous droplets via continued generation of the circulating flow pattern.

The developing step may include the step of directing a positive thermal flux and a negative thermal flux toward the gas-liquid interface of the non-aqueous liquid film to create a surface tension profile.

In accordance with yet another aspect of the disclosure, a method of controlling flow in a liquid film includes developing a variation in surface tension at a gas-liquid interface of the liquid film with a non-heated manipulation tool, and generating a flow pattern within the liquid film by maintaining the surface tension variation at the gas-liquid interface of the liquid film.

In some cases, the developing step includes the step of suspending a non-heated probe above the gas-liquid interface of the liquid film. The developing step may then further include the step of suspending a heated probe above the gas-liquid interface of the liquid film to create a surface tension profile. One of the non-heated and heated probes may include a line-shaped tip.

In accordance with still another aspect of the disclosure, a method is useful for flow control within a droplet suspended within a liquid film. The method includes the steps of directing a source of energy toward the droplet, and generating a flow pattern within the droplet by maintaining the directing step.

In some cases, the liquid film has a depth approximately equal to a diameter of the droplet.

The energy source may include a microprobe tip having a diameter smaller than a diameter of the droplet. Alternatively, the energy source includes a microprobe tip having a diameter similar in size to a diameter of the droplet such that the generating step rotates the droplet.

In some embodiments, the energy sources includes a probe tip and the directing step includes contacting the liquid film with the probe tip.

In accordance with yet another aspect of the disclosure, an apparatus is useful for collecting suspensions in a liquid film. The apparatus includes a platform to support the liquid film, a probe tool device suspended above the platform in proximal relation to a gas-liquid interface of the liquid film, and a scanning stage for relative movement of the platform and the probe tool to define an area of the liquid film from which the suspensions are collected. The probe tool device includes an energy source to project a variation in surface tension on the gas-liquid interface.

In some embodiments, the probe tool device includes a thermal energy source. The thermal energy source may be configured to project negative thermal energy toward the gas-liquid interface of the liquid film.

Alternatively, the probe tool device includes an electric field source.

In some cases, the apparatus further includes a collection device having receptors disposed in the liquid film and configured to capture the suspensions.

BRIEF DESCRIPTION OF THE DRAWING FIGURES

For a more complete understanding of the disclosure, reference should be made to the following detailed description and accompanying drawing figures, in which like reference numerals identify like elements in the figures, and in which.

Figure 1:
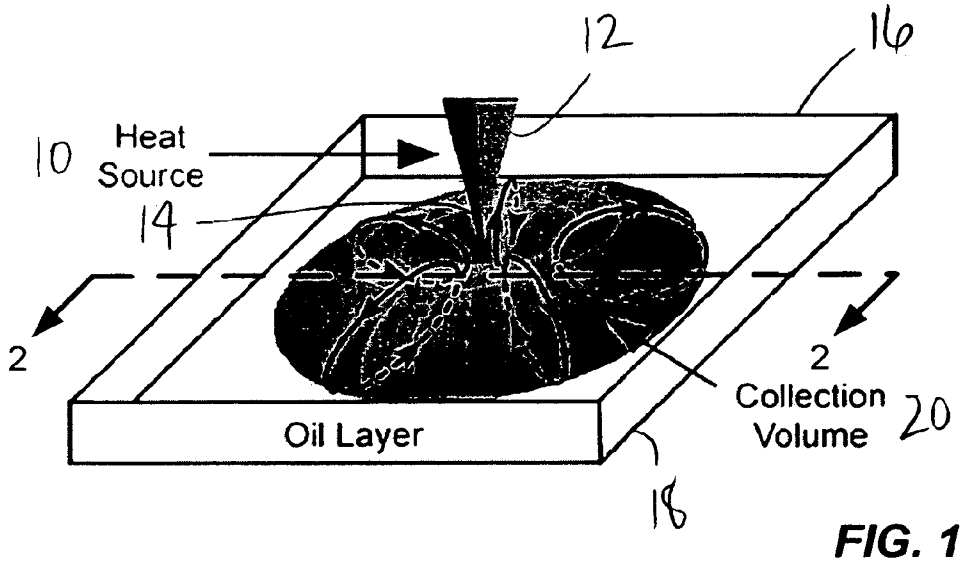
FIG. 1 is a schematic representation of a surface-tension variation technique for liquid flow manipulation and control in accordance with one aspect of the disclosure.

While the disclosed methods and apparatus are susceptible of embodiments in various forms, there are illustrated in the drawing (and will hereafter be described) specific embodiments of the invention, with the understanding that the disclosure is intended to be illustrative, and is not intended to limit the invention to the specific embodiments described and illustrated herein.

DETAILED DESCRIPTION OF PREFERRED EMBODIMENTS

Generally speaking, disclosed herein are liquid flow manipulation and control techniques based on the variation of surface tension at a gas-liquid interface. In some cases, the techniques involve the control of liquid flow to collect particulates and other suspensions within the liquid. The suspensions may, for instance, include or involve microparticles (e.g., molecules) or microdroplets that, in turn, may encapsulate further elements of interest. In these and other ways, the disclosed techniques are well suited for use in biological and chemical diagnostics and other applications, such as DNA harvesting. However, practice of the disclosed techniques are not limited to such applications or contexts.

As described below in connection with some embodiments, high-speed toroidal flows and other flow patterns can be generated via the disclosed techniques, and the shape and speed of the flow patterns can be controlled. With the circulating nature of the toroidal flow patterns, microparticles, microdroplets and other suspensions within the liquid can be trapped and manipulated. The manipulation or other processing of the suspensions may be conducted on unpatterned and otherwise straightforward substrates (e.g., a glass slide). As a result, the disclosed techniques do not necessarily require a microfluidic chip, or textured or other patterned substrate involving, for instance, regions of hydrophilic and hydrophobic surfaces to direct the liquid flows. That said, practice of the disclosed techniques may still be implemented in conjunction with such substrates and microchips, as desired. For instance, use of the disclosed techniques in conjunction with such substrates and microchips may combine the benefits and functionality provided by both approaches to liquid flow control and microfluidics, but without various disadvantages, such as the significant loss of heat to the substrate in prior thermal-based flow control techniques.

In accordance with some aspects of the disclosed techniques, the manipulation and control of liquid flow is achieved without physical contact with the liquid. More specifically, the tools, devices, apparatus or other mechanism involved in directing the variations in surface tension need not contact the liquid, but rather remain suspended above the gas-liquid interface. As described below, such tools may include a heated (or cooled) probe suspended above the liquid surface such that a tip of the probe is in proximal relation to the liquid.

For the foregoing and other reasons described herein, the tool, device or other apparatus directing the surface tension variation can be scanned over or across the surface of the liquid using, for instance, an XY scanning stage, to effect and control movement and re-positioning of the flow patterns within the liquid. Any suspensions circulating in the flow pattern remain entrapped as the flow pattern is moved, and further suspensions may be collected. As described below, this scanning and collection technique may be useful in variety of contexts and applications.

The disclosed techniques are well suited to driving micro-scale currents in an oil phase, or oil film. Here, the disclosed techniques may involve methods to generate steady state micro-scale currents within oil using thermal convection. Notwithstanding the advantages of using oil as a medium for biological and chemical analyses and other work, practice of the disclosed techniques is not limited to any one liquid medium.

With reference now to the drawing figures, FIG. 1 illustrates an exemplary embodiment in which a heat (or other energy) source (or sink) indicated generally at 10 includes, for instance, a microfabricated probe 12 having a tip 14 suspended above a surface 16 of a liquid film or layer 18. In this case, the liquid film 18 is a layer of oil that may (but need not) be, for purposes of the disclosed techniques, an unconstrained thin film. In this sense, the film 18 may be a thin layer of oil placed on, for instance, a glass slide 19 (see FIG. 2).

With the heat source 10 activated, flows are generated beneath the heat source 10 in the liquid film 18 as shown schematically and generally as a volume 20. The flow pattern of the volume 20 includes outward flow at or near the surface 16, and inward flow below the surface 16, to create a self-contained, circulating flow pattern as shown. As a result, any particles or other elements present in the volume 20 may become trapped in the circular flow. In this case, the volume 20 is a toroidal flow pattern, such that the volume 20 amounts to a collection area or region extending radially from the point beneath the probe 12.

Figure 2:
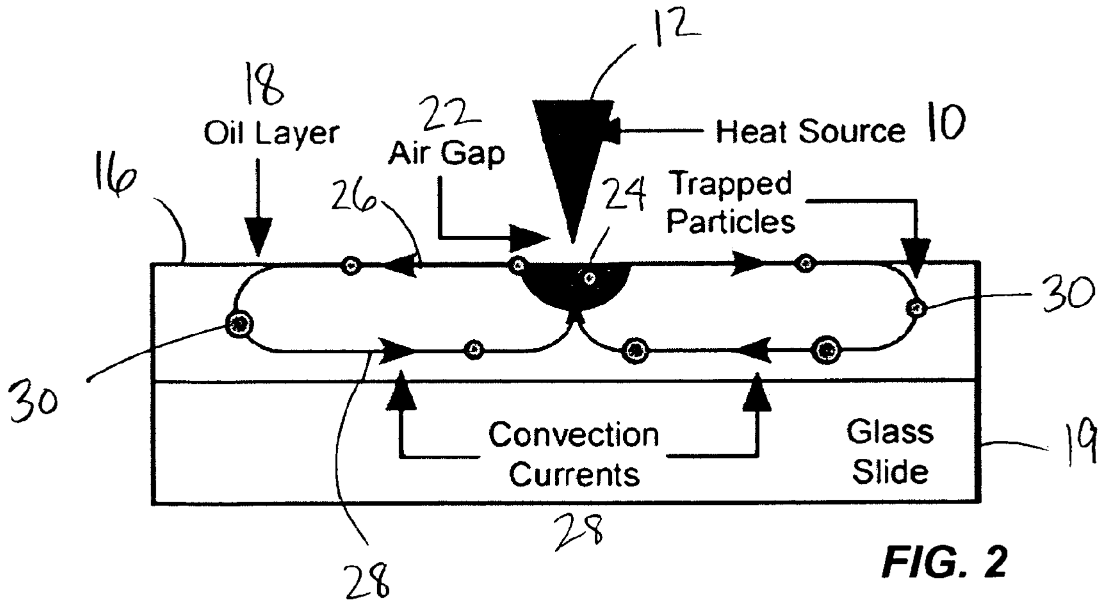
FIG. 2 is a sectional, schematic view of a flow pattern generated in accordance with the technique of FIG. 1 taken along the line 2-2 of FIG. 1.

FIG. 2 shows the flow pattern of FIG. 1 in greater detail. When the separation between the heat source 12 and the oil surface 16 is sufficiently low (e.g., less than about 400 μm), heat transferred through a thin air gap indicated generally at 22 to a small region on the oil surface drives currents in a small region 24 beneath the heat source 12. Within this region 24, liquid flows vertically upwards, resulting in an outward flow 26 at the top surface 16 of the liquid and an inward flow 28 below the surface 16. Together, the surface and subsurface currents 26, 28 form a circular vortex in which particles 30 may be trapped. Observed in three-dimensions, the flow pattern is a toroid centered below the heat source 12.

The flow pattern is similar to a single Rayleigh-Bénard cell in which the convection rolls are radially oriented. However, the physical effect driving the flow involves surface tension, often referred to as Bénard-Marangoni convection, where the local surface tension of the oil decreases due to the temperature increase, resulting in Marangoni forces which drive the outward flow 26 on the top surface 16. Such surface tension driven effects may tend to dominate in thin layers of liquid. More generally, the disclosed techniques involve or incorporate aspects of the Marangoni effect, where mass transfers occur on, or in, a liquid layer due to surface tension differences. In this effect, a surface tension gradient causes liquid to flow away from regions of low surface tension. Surface tension generally arises from intermolecular forces within the liquid that cause the liquid to, in effect, squeeze itself together to minimize surface area. In this exemplary case, a variation in temperature at the gas-liquid interface results in a localized variation of the surface tension on the liquid surface. In other cases, other mechanisms (e.g., electric field distributions) may contribute to the variation of the surface tension.

In embodiments utilizing temperature variation as the variation mechanism, a variety of different tools, probes or other devices may be used as the heat source 10 (or any component thereof), including for instance, an atomic force microscopy (AFM) or similar thermal scanning microscopy probe, as well as the micromachined thermal probe described in U.S. Pat. No. 6,692,145 entitled "Micromachined Scanning Thermal Probe Method and Apparatus," the disclosure of which is hereby incorporated by reference in its entirety. For further information regarding a suitable probe for use in the disclosed techniques, see also Li, et al., "Applications of a low contact force polyimide shank bolometer probe for chemical and biological diagnostics," Sensors and Actuators A, vol. 104, pp. 236-245 (2003), the disclosure of which is also hereby incorporated by reference in its entirety. In these exemplary cases, the probe 12 includes a gold thin film heater (not shown) embedded at the tip of a polyimide cantilever (not shown). Electrical connection is provided by thicker metal lines running the length of the cantilever. Due to the low thermal conductivity of polyimide, the probes can be heated to 250° C. with less than 20 mW input power. Exemplary probes may be about 120 μm in width, 360 μm in length, and have resistances ranging from 25-35 ohms.

Experiments utilizing such probes have exhibited the controlled generation of toroidal flows in various oils including commercially available mineral oil, olive oil, and kerosene oil. In each of these experiments, a 250 μL sample of oil was spread on a glass microscope slide to achieve the desired thickness (or depth), which may fall within a broad range, including, for instance, 10-1000 μm, and, in the examples described herein, about 80 to about 400 μm. In several cases, particles were used to illustrate the flow and the manner in which the particles are trapped within the flow. In one experiment, commercially available weed pollen with an approximate 30 μm diameter was immersed in mineral oil. Video images obtained using a CCD camera were analyzed frame by frame to determine the position of a selected particle at 1/30 second intervals. The radial position of a typical particle was measured for 4.7 seconds, corresponding to two full cycles. Qualitatively, the particles traveled away from the heat source on the top surface of the oil, slowing gradually. Eventually, the particles reaches zero velocity at the outer edge of the collection region, at which point each particle sinks to the bottom of the oil layer and is accelerated inward. Upon reaching the center of the vortex beneath the heat source, the particle rises quickly to the surface and attains maximum lateral velocity as it is propelled outward.

Calculations of the instantaneous radial velocity showed that the liquid velocity field is steady state both spatially and temporally. The flow velocities were determined primarily by the liquid temperature, which in turn may be controlled by the heat transferred to the oil surface. In the case of the thermal probes, the degree of heat transfer was determined by two factors: (1) the temperature of the cantilever tip, which may be proportional to the input power (see references cited above); and, (2) the distance between the cantilever and the surface of the oil. Flow velocities were measured at various powers and air gaps, and it was found that velocities increase linearly with respect to input power, and decay exponentially as the probe is moved away from the liquid surface. Velocities also depend on the viscosity and thickness of the oil layer, and, to a lesser degree, the ambient temperature.

While the speed can be tailored through the control of the surface temperature, it was observed that, for a given oil, the radius of the collection region is set by the thickness of the liquid layer. In fact, the radius of the toroid scales as a power function of the oil layer thickness.

Figure 3:
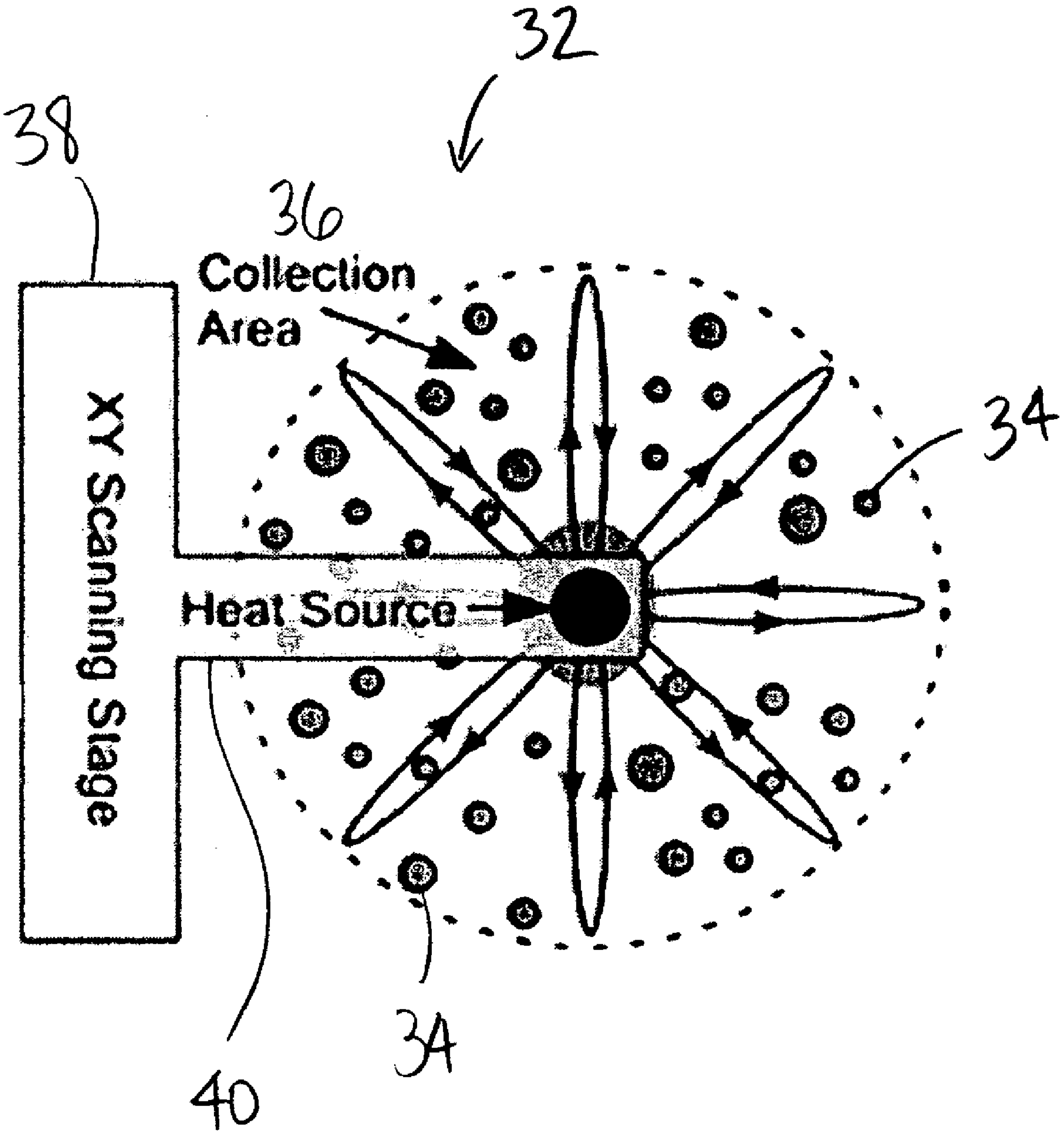
FIG. 3 is schematic representation of a collection apparatus implementing a collection technique in accordance with further aspects of the disclosure.

With reference now to FIG. 3, one application of the toroidal flow pattern and flow generation technique described above is shown via an apparatus indicated generally at 32 and configured for collection of particulates 34 and other suspensions (e.g., droplets) in a liquid film disposed on a platform, such as the glass slide 19 (FIG. 2). These aspects of the disclosure apply the disclosed flow control techniques to collect the particulates 34 and other suspensions within a collection area or region indicated generally at 36 that is scanned across or over the liquid sample medium. In one sense, this collection technique generally utilizes the self-contained, or circulating, nature of the flow pattern, as well as the ability to move the flow pattern without disruption of its containment of the suspensions entrapped within it. To that end, the apparatus 32 includes a scanning stage 38 coupled to the heat source 10 (FIGS. 1 and 2) and the probe 12 via an arm (or other projection) 40 that may assist in the suspension of the probe 12 above the liquid film. Generally speaking, the scanning stage 38 supports relative movement of the probe 12 and the platform upon which the liquid sample is disposed. The scanning stage 38 may thus adjust the two-dimensional (i.e., XY) position of the probe 12 over the liquid surface to move the collection area 36. In this way, the entire liquid sample may be scanned, capturing and entrapping the suspensions encountered along the way.

The operation of the apparatus and the implementation of this collection technique has been illustrated by the trapping of airborne particulates, such as weed pollen. The technique has also been demonstrated via the collection of microdroplets, where 5 μL of water was pipetted into an oil sample and stirred vigorously to produce droplets with radii ranging from 5-100 μm. Small droplets tended to travel the entire convective flow path, whereas larger droplets traveled smaller paths.

Any type of heat source (or sink) that heats (or cools) the surface of the liquid may be utilized, and need not involve a microprobe. For instance, some embodiments may utilize a heated needle (e.g., 15 μm tip). In other cases, the heat source need not include a device having a tip. Heat sources may thus take on different shapes other than point sources, such as curved or straight lines, areas, or any combination thereof. Other heat sources may not involve a structural projection, but nonetheless involve one or more of the following: (i) the projection of energy toward the liquid surface, (ii) the creation of a spatially varying, or localized source of energy, and (iii) a re-distribution of energy at the gas-liquid interface. Examples include lasers, used either alone or in conjunction with absorbent beads or other materials designed to absorb laser energy. Other sources or source mechanisms include surface heating (or cooling) via convection (e.g., shooting hot air at liquid surface) or other convection-based techniques, and condensation of a liquid adding the latent heat of vaporization to the liquid (especially in aqueous samples). More generally, any heating (or cooling) device(s) that creates surface temperature changes resulting in a surface tension variation can result in flow in accordance with the disclosure. As described below, other, non-heated thermal-based actuation mechanisms may also or alternatively be used. More specifically, the thermal-based actuation of the flow patterns may result from negative heat sources, i.e., cold sources, or heat sinks deployed in a manner similar to the heat sources described above. In these cases, the flow patterns may generally remain the same, albeit with reversed flow directions.

In fact, practice of the disclosed techniques is not limited to thermal sources, but rather may involve other sources of energy directed to varying the surface tension of the liquid. For example, one such alternative, non-heated source may vary the surface tension via an electric field.

Regardless of the manner in which the surface tension variation is effected and maintained, the source(s) of the variation may be used to generate micro-scale toroidal flows in which particles and microdroplets are deliberately trapped. The speed of the flow pattern may be tuned by adjusting the source, while the radius may be set by the thickness of the oil layer. Because the source does not make physical contact with the liquid, it allows the flow pattern(s) (e.g., vortices) to be scanned across the liquid surface for collection and entrapment of particulates and other suspensions disposed throughout the sample.

Figure 4:
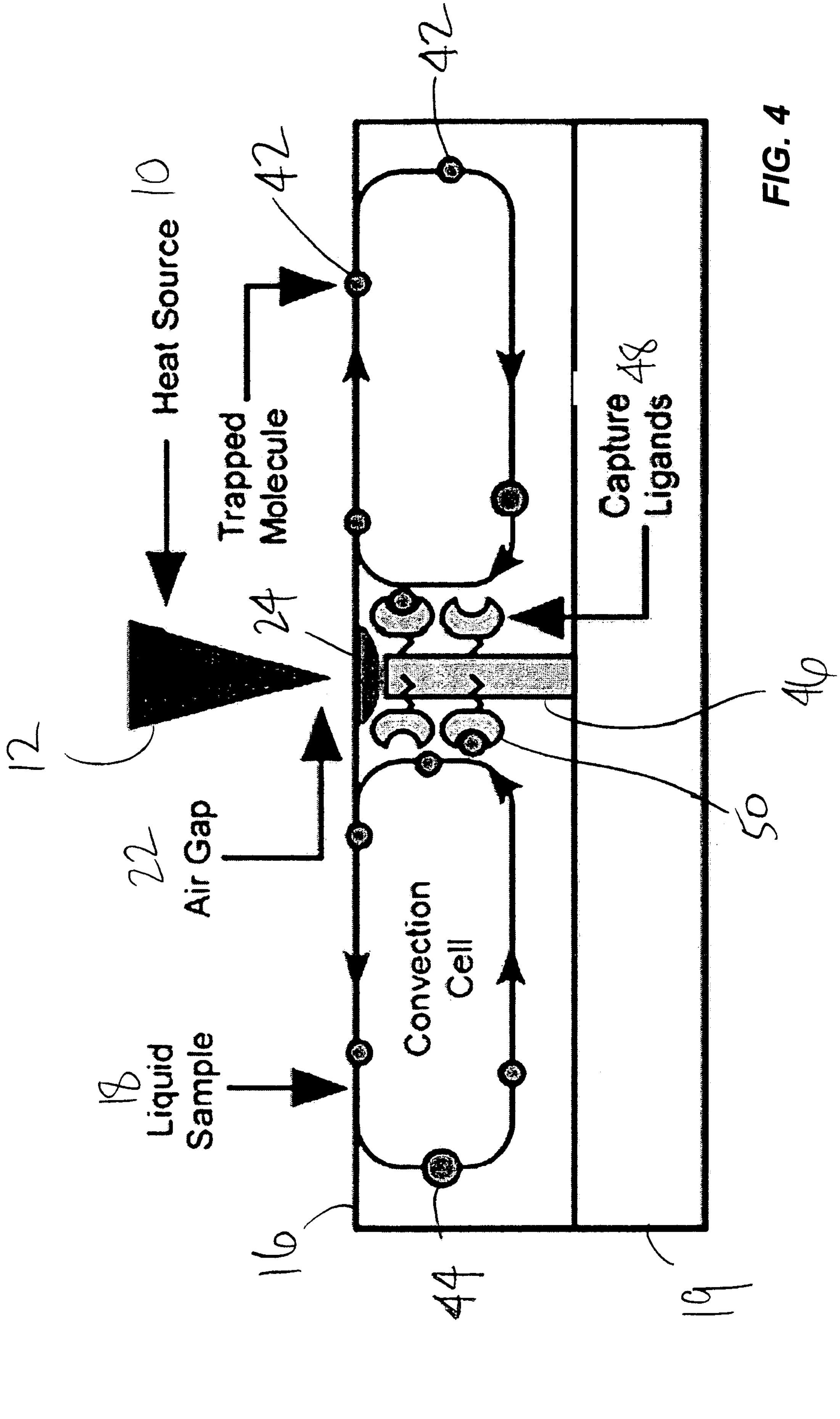
FIG. 4 is a schematic representation of a portion of the collection apparatus of FIG. 3 in accordance with one embodiment.

Generally speaking, the flows created using the disclosed techniques may be tailored to achieve a variety of different biological, chemical or other analytical procedures involving the liquid or any elements suspended within it. To this end, the disclosed techniques may be used to specify the speed and geometry of the flow pattern(s) to accommodate specific procedures such as single molecule detection (SMD) procedures. FIG. 4 depicts an exemplary embodiment that exhibits these advantages of the disclosed techniques. In order for a molecule, particle, etc. to be captured, it often may involve contact with a solid surface presenting ligands or other chemistry with which the molecule can bond. In common microfluidic platforms, the sample solution makes a single pass over the capture region presented by the solid surface. In other cases, simple, random diffusion processes are relied upon to enable the contact. As shown in FIG. 4, the disclosed techniques in contrast provide a self-contained, circulating flow pattern that causes the molecules entrapped within the flow to repeatedly pass over the capture region, thereby enhancing the likelihood and capability of molecule detection.

Specifically, the exemplary embodiment of FIG. 4 depicts a schematic cross-section of a molecular detection technique using Marangoni flows where a micro-scale heat source (e.g., the heat source 12) is suspended above a thin liquid layer (e.g., the liquid sample 18) to heat a small region (e.g., the area 24) of the liquid surface 16. Surface tension gradients caused by the temperature change drive liquid outwards on the surface, and inwards below the surface. The resulting, self-circulating flow eventually encounters molecules 42, 44 of interest, either through scanning or other procedures, corralling the molecules 42, 44 in the self-circulating flow until capture occurs. To that end, a small post 46 or other structure is placed in the liquid film 18 at a convenient location. Because the flow pattern may be scanned, the location need not be directly below the heat source 10 as shown, but rather may proceed to that location after, for instance, scanning of the sample. In any case, the post 46 presents functionalized ligands 48, 50 configured to capture the molecules 42, 44, respectively.

In accordance with other aspects of the disclosure, application of the disclosed techniques may involve mixing, concentration and harvesting of molecules, particulates and other suspensions from a liquid sample. In some cases, these suspensions may include or involve microdroplets in which particles may be suspended. For example, microprobes may be used to manipulate, concentrate, and sample aqueous droplets within an oil phase on a blank substrate. In these and other cases, a point heat source may perform high speed mixing of droplets at speeds of hundreds of revolutions per minute (e.g., up to 300 rpm), collection and merging of droplets, concentration of suspended particles through controlled evaporation of the droplet, and precipitation of low concentration suspensions such as DNA onto a microprobe tip. Experiments using the techniques described below have shown that quantities of DNA as low as 10 ng have been sampled on a 15 μm diameter tip.

Another aspect of the disclosure is directed to supporting, for instance, microscale investigations in cellular and biochemical analyses involving microdroplet-based schemes. These schemes may employ microdroplets as microscale reactors for quantifying, for instance, single cell enzyme kinetics, concentrating nanoparticles and dissolved solutes, detecting low concentrations of molecules, and amplifying single molecules, such as DNA. Described below are a number of micro-thermal techniques to support such analyses in microdroplet schemes, all of which make use of a heated microprobe tip or other heat source (as described above). Specifically, these techniques enable, either alone or in combination with other aspects of the disclosure, the high speed mixing of droplets, collection and merging of droplets, concentration of suspended particles, and the aggregation of DNA onto a microprobe tip.

Figure 5:
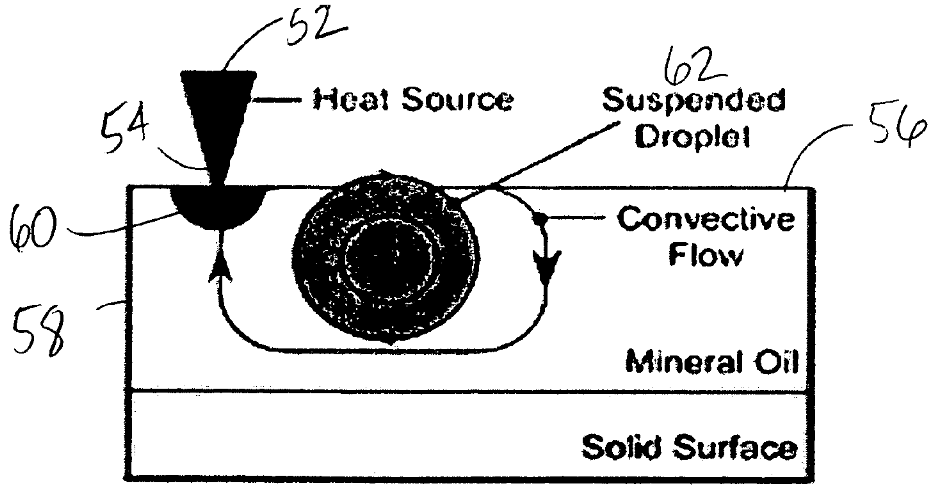
FIG. 5 is a schematic representation of a liquid flow manipulation and control technique involving a suspended droplet in accordance with another aspect of the disclosure.

Convective Mixing Of Droplets. In the exemplary embodiment illustrated in FIG. 5, a heat source 52 having a heated metal tip 54 (e.g., $\phi$=5-620 μm, T=35-45° C.) placed in contact with a surface 56 of a thin layer 58 of mineral oil (e.g., 200-1500 μm) establishes a micro-scale temperature gradient extending radially from a region 60 directly beneath the heat source 52. The resulting currents flow radially outward on the top surface 56 of the liquid pool 58, and inward below the surface 56, forming self-circulating toroidal streamlines (as described above). In the above-described embodiments, however, the particles are small compared to the cross-sectional height of the convective flow region and, as a result, they follow the toroidal streamlines. In this case, the height of the flow region is approximately the same as the diameter of a droplet 62 suspended in the liquid 58.

Figure 6:
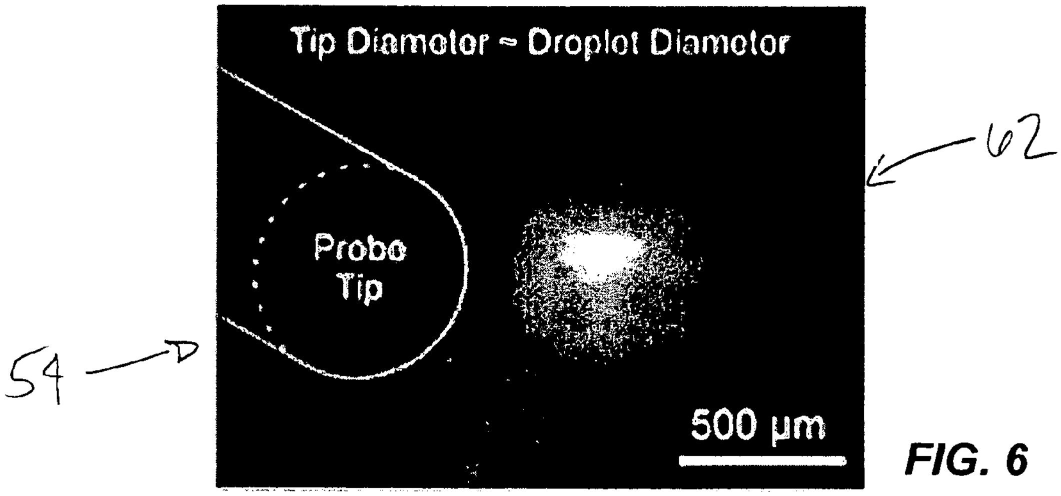
FIGS. 6 and 7 are photographic representations of the flow manipulation technique of FIG. 5 in accordance with alternative embodiments involving differently sized probe tips; and, FIG. 8 is a schematic representation of a liquid flow manipulation and control technique in accordance with another aspect of the disclosure.
Figure 7:
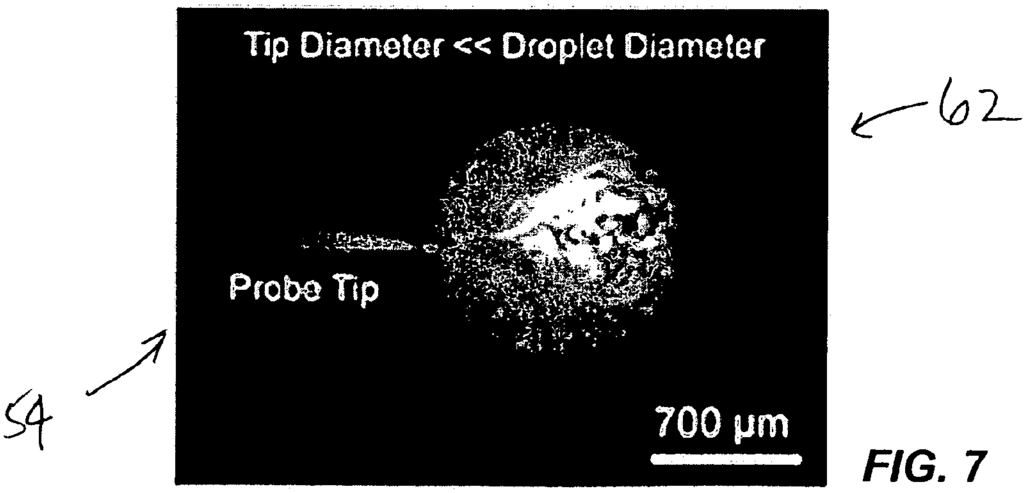

As a result of the relative sizes of the droplet 62 and flow region, the currents rotate and mix the droplet 62 in various patterns as a function of the size of the heated tip 54. In cases where the tip diameter is approximately the same size as the droplet 62, as shown in FIG. 6, the droplet 62 rotates about a single axis at speeds up to, for instance, 300 rpm. As the droplet diameter is progressively increased, the rotational speeds fall, and the flow pattern begins to change. As shown in FIG. 7, eventually, when the tip diameter is small (e.g., about 15 μm) compared to the droplet 62 (e.g., about $\phi$=1000 μm), a flow pattern composed of two vortices and turbulent eddies is observed instead of rotation. Both of the patterns shown in FIGS. 6 and 7 can be useful for micro-mixing within a single droplet. In the experiments that led to the patterns shown in FIGS. 6 and 7, the tip temperature was approximately 35-45° C., and the flow patterns were visualized using immersed fluorescein particles and a 0.5 second CCD exposure with 490 nm/500 nm excitation/emission filters. Other temperatures and operational parameters may alternatively be used.

Droplet Collection and Merging. The above-described scanning techniques may be applied to droplet collection and merging. The ability to merge discrete droplets is often used in microdroplet systems, as it allows reagents to be mixed at time scales fast enough to study chemical kinetics. To collect and merge droplets, a heated tip (e.g., similar to those described above) is suspended just above the oil layer, and heat transferred to the oil surface drives currents in the same manner as described above. Droplets trapped in the flow collide and merge together without the aid of a surfactant. The circulation (or other motion) and reduced surface tension due to heating may both assist in droplet merging. By scanning the heat source laterally, several droplets over a large area can be collected and merged.

Concentration of Suspended Particles. Unlike droplet evaporation on a solid surface, where suspended particles eventually deposit themselves in a circle (the commonly observed "coffee ring" result), particles in an oil immersed microdroplet aggregate towards the center instead, eventually forming a concentrated solid precipitate after the liquid has completely evaporated. Microdroplet evaporation is, therefore, an effective means to concentrate particles dissolved solutes, but evaporation times for even small ($\phi$=10 μm) droplets can be greater than one hour.

In accordance with another aspect of the disclosure, a heated tip (similar to those described above) placed next to a suspended microdroplet enhances the evaporation rate, allowing controlled evaporation of an 1800 μm droplet in less than 3 minutes. After the droplet has evaporated, the concentrated solids remain in the oil, trapped in the convective flow described above. The suspended microdroplet may have been collected at the outset via the techniques described above.

In one example, a 60° C., 50 μm tip is placed in contact with the oil near an 1800 μm droplet containing suspended 3 μm polystyrene beads. As the liquid evaporated, the dissolved particles concentrated in the center of the droplet, forming a solid micro-particle suspended in the oil. The surface area of the droplet decreased linearly with time until all the liquid was evaporated at 150 s.

Aggregation DNA on a Microprobe Tip. An extension of the foregoing technique involves microprobe and other devices having suitably sized tips for interaction with the suspended droplets. In these cases, a droplet may be evaporated with the heated tip immersed within it, such that any suspended or dissolved compounds aggregate on the tip as the droplet evaporates. This technique provides a mechanism for concentrating and sampling small amounts of solutes (e.g., 'nanosampling') onto a probe tip for subsequent analysis using methods such as micro-IR spectroscopy.

Further aspects of the disclosure involve other techniques based on evaporation effected by the proximity of the above-described thermal devices. One application of these techniques involves controlling the deposition or collection of DNA and other solutes. Usually, DNA is 'spotted' on microarrays by drying a droplet of DNA-containing solution on a flat substrate. When drying, capillary forces cause the DNA to deposit in a ring around the perimeter of the droplet when it has completely evaporated. This occurs because evaporation rates at the droplet edges are higher than the evaporation rate at the droplet center. By placing the heat source above the center of the droplet, evaporation rates are highest at the center, and capillary flow may be directed inward instead. DNA is deposited in a spot instead of a ring, and this is thought to increase sensitivity in microarray experiments.

More generally, these aspects of the disclosure may involve the creation of evaporation flux profiles (i.e., localized evaporation) on a liquid surface, in a manner somewhat similar to the creation of the localized temperature gradients at the gas-liquid interface for flow generation as described above. In fact, such profiles may be developed the same way as the thermal profiles are developed as described above. For example, if we place a thermal probe near the surface, evaporation rates are enhanced at the surface near the probe. Accordingly, in some cases, this evaporation technique may be combined with the liquid actuation and suspension collection techniques described above.

These evaporation-based techniques may be useful, for instance, in single molecule detection schemes. If a very small heat source is used, the spot size can be very small. This may result in the deposition of molecules into a very small region (i.e., a concentration location) which could later be imaged. For instance, a heat source suspended above a droplet or liquid film may be used to increase the evaporation rate in its vicinity. As described above, the heat source may be an atomic force microscopy probe with heating capabilities. Positioning the heat source near the liquid surface until the droplet/film has completely evaporated may include or involve moving the heat source gradually towards the flat surface as the droplet evaporates. As a result, the molecules deposit themselves in a spot directly beneath the heat source. The spot may then be using a high resolution imaging technique, such as atomic force microscopy (AFM), to visualize molecules. If the heat source was a heated atomic force microscopy probe, then the probe would already be positioned in the correct location, i.e., the concentration location, for scanning. Generally speaking, this technique may support the localization and further processing (e.g., imaging) of individual molecules in low concentration solutions.

Figure 8:
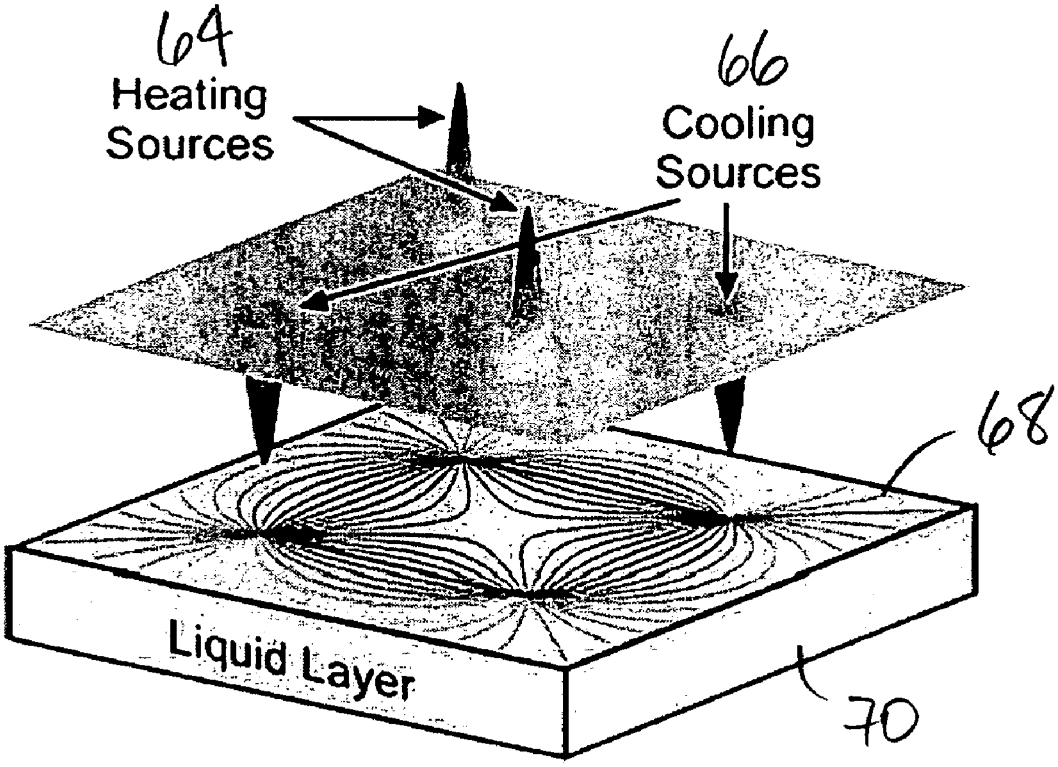

FIG. 8 illustrates the generation of a flow pattern in accordance with the disclosed techniques and, specifically, how multiple sources and sinks can result in more generalized and complex flow patterns. Indeed, any desired flow pattern may be realized given a particular distribution or profile of surface tension affecting energy sources. In a sense, the patterned heat distribution established by the source(s) and/or sink(s) bring about a corresponding patterned flow within the liquid film. In this exemplary case, a plurality of thermal sources, including heating sources 64, and cooling sources 66, generate a contribution to the temperature gradients on a liquid surface 68 of a liquid layer 70. As a result, any type of flow can be realized by heating and cooling different regions of the liquid surface. For example, a cold probe has been shown to develop a flow pattern having a toroid cell with a direction reversed from that developed with a heated probe.

In embodiments involving or including oil in the liquid film or medium, a variety of different oils may be used such that the disclosed techniques are not limited to the exemplary embodiments described herein. For instance, mineral or biological oils may be used, as desired. More generally, practice of the disclosed techniques is not limited to any one particular oil type, such as triglycerides and other hydrocarbons. In fact, other low volatility liquids may be utilized in alternative embodiments.

Although the foregoing exemplary embodiments are described in connection with surface tension variations as the primary mechanism for liquid flow manipulation and control, practice of the disclosed techniques may be complemented by or otherwise used in combination with other flow control mechanisms and forces, such as gravitational forces, convective forces, etc. Similarly, any desired substrate, microfluidic chip or other structure (e.g., a microchannel) may be used in conjunction with such mechanisms and forces to achieve desired flow patterns and/or liquid suspension collection or other manipulation. Still further, the disclosed techniques may be used in combination with surfactant-based techniques for additional manipulation or control of the liquid flow via complementary or alternative surface tension variations effected by the surfactant(s). For these reasons, practice of the disclosed techniques is not limited to the manipulation and control of flow within unconstrained liquid films (as described above), but rather may be complemented in a variety of ways with force-based, structural, chemical or other mechanisms to achieve a desired liquid actuation scheme.

Flow manipulation and actuation has been described above in connection with flow patterns that may be used for trapping, mixing, and spinning aqueous microdroplets and other suspensions encapsulated in a sample medium. Examples have involved linear flow velocities can approach 5 mm/s in doublet flow, and 2 mm/s in toroidal flow. The doublet flow has exhibited two steady state vortices with rotational velocities of, for instance, about 1200 rpm on length scales of 20-50 μm, making it useful for high-speed laminar mixing. Temperature elevations in the liquid for these examples were estimated to be <2° C.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding only, and no unnecessary limitations should be understood therefrom, as modifications within the scope of the invention may be apparent to those having ordinary skill in the art.

What is claimed is:

1. A method of collecting suspensions in a liquid film, the method comprising the steps of:

developing a variation in surface tension at a gas-liquid interface of the liquid film to generate a circulating flow pattern within the liquid film; and, scanning the liquid film with the circulating flow pattern for entrapment of the suspensions in the flow pattern by re-directing the variation in the surface tension across the gas-liquid interface of the liquid film.

2. The method of claim 1, wherein the suspensions comprise emulsified droplets.

3. The method of claim 2, further comprising the step of maintaining the variation in the surface tension at the gas-liquid interface to merge the emulsified droplets entrapped in the circulating flow pattern.

4. The method of claim 1, wherein the developing step comprises projecting a thermal flux toward the gas-liquid film.

5. The method of claim 4, further comprising the step of enhancing evaporation of the liquid by maintaining the projecting step.

6. The method of claim 5, wherein the evaporation enhancing step comprises forming residue from the suspensions at a concentration location.

7. The method of claim 6, wherein the evaporation enhancing step comprises directing an atomic force microscopy (AFM) probe as a heat source toward the concentration location, and wherein the method further comprises the step of obtaining an image using the AFM probe of the residue at the concentration location.

8. The method of claim 1, further comprising the step of collecting the suspensions by exposing the entrapped suspensions to a collection apparatus comprising receptors configured to collect the suspensions.

9. The method of claim 8, wherein the receptors comprise ligand molecules.

10. The method of claim 9, wherein the suspensions comprise DNA molecules.

11. The method of claim 1, wherein the circulating flow pattern comprises a toroidal cell.

12. The method of claim 1, wherein the liquid comprises an oil.

13. A method of controlling flow in a non-aqueous liquid film, the method comprising the steps of:

developing a variation in surface tension at a gas-liquid interface of the non-aqueous liquid film; and, generating a flow pattern within the non-aqueous liquid film by maintaining the surface tension variation at the gas-liquid interface of the non-aqueous liquid film.

14. The method of claim 13, wherein the developing step comprises the step of projecting a thermal flux between the gas-liquid interface of the non-aqueous liquid from a source suspended above the gas-liquid interface of the non-aqueous liquid.

15. The method of claim 14, wherein the projecting step comprises the step of positioning a thermal probe in proximal relation to the gas-liquid surface.

16. The method of claim 13, wherein the developing step comprises the step of modifying the surface tension at the gas-liquid interface with an electric field.

17. The method of claim 13, wherein the developing step comprises the step of suspending a probe above the gas-liquid interface, and wherein the method further comprises the step of re-positioning the probe to move the flow pattern across the non-aqueous liquid film.

18. The method of claim 17, further comprising the step of entrapping suspensions in the non-aqueous liquid film within the flow pattern.

19. The method of claim 18, further comprising the step of depositing the entrapped suspensions in receptors configured to collect the entrapped suspensions.

20. The method of claim 19, wherein the receptors comprise ligand molecules.

21. The method of claim 20, wherein the suspensions comprise DNA molecules.

22. The method of claim 13, wherein the non-aqueous liquid comprises an oil.

23. The method of claim 22, wherein aqueous droplets are emulsified in the oil and trapped within the flow pattern.

24. The method of claim 23, wherein the generating step comprises the step of merging the aqueous droplets via continued generation of the circulating flow pattern.

25. The method of claim 13, wherein the developing step comprises the step of directing a positive thermal flux and a negative thermal flux toward the gas-liquid interface of the non-aqueous liquid film to create a surface tension profile.

26. A method of controlling flow in a liquid film, the method comprising the steps of:

developing a variation in surface tension at a gas-liquid interface of the liquid film with a non-heated manipulation tool; and, generating a flow pattern within the liquid film by maintaining the surface tension variation at the gas-liquid interface of the liquid film.

27. The method of claim 26, wherein the developing step comprises the step of suspending a non-heated probe above the gas-liquid interface of the liquid film.

28. The method of claim 27, wherein the developing step further comprises the step of suspending a heated probe above the gas-liquid interface of the liquid film to create a surface tension profile.

29. The method of claim 28, wherein one of the non-heated and heated probes comprises a line-shaped tip.

30. A method of flow control within a droplet suspended within a liquid film, the method comprising the steps of:

directing a source of energy toward the droplet; and, generating a flow pattern within the droplet by maintaining the directing step.

31. The method of claim 30, wherein the liquid film has a depth approximately equal to a diameter of the droplet.

32. The method of claim 30, wherein the energy source comprises a microprobe tip having a diameter smaller than a diameter of the droplet.

33. The method of claim 30, wherein the energy source comprises a microprobe tip having a diameter similar in size to a diameter of the droplet such that the generating step rotates the droplet.

34. The method of claim 30, wherein the energy sources comprises a probe tip and the directing step comprises contacting the liquid film with the probe tip.

* * * * *